(12) United States Patent
Kerrouche et al.

(10) Patent No.: US 12,064,263 B2
(45) Date of Patent: Aug. 20, 2024

(54) CONNECTED BRACELET TYPE DEVICE FOR INDIVIDUAL MONITORING AND METHOD FOR MONITORING A USER

(71) Applicants: Samira Kerrouche, Garges-les-Gonesse (FR); Hayame Bouyahia, Franqueville Saint Pierre (FR)

(72) Inventors: Samira Kerrouche, Garges-les-Gonesse (FR); Hayame Bouyahia, Franqueville Saint Pierre (FR)

( * ) Notice: Subject to any disclaimer, the term of this patent is extended or adjusted under 35 U.S.C. 154(b) by 322 days.

(21) Appl. No.: 17/239,541

(22) Filed: Apr. 23, 2021

(65) Prior Publication Data

US 2021/0330257 A1   Oct. 28, 2021

(30) Foreign Application Priority Data

Apr. 23, 2020   (FR) ...................................... 20 04050
Apr. 23, 2020   (FR) ...................................... 20 04051

(51) Int. Cl.
*A61B 5/00* (2006.01)
*A61B 5/01* (2006.01)
(Continued)

(52) U.S. Cl.
CPC ............ *A61B 5/681* (2013.01); *A61B 5/0022* (2013.01); *A61B 5/01* (2013.01); *A61B 5/02055* (2013.01);
(Continued)

(58) Field of Classification Search
CPC ........... A61B 5/681; A61B 5/01; A61B 5/024; A61B 5/026; A61B 5/14542;
(Continued)

(56) References Cited

U.S. PATENT DOCUMENTS

2005/0038345 A1*   2/2005   Gorgenberg ......... A61B 5/0265
600/502
2007/0273504 A1*  11/2007   Tran .................... A61B 5/7405
340/539.12

(Continued)

FOREIGN PATENT DOCUMENTS

CH         703 352 A1    12/2011
EP       1 918 191 A1     5/2008
(Continued)

OTHER PUBLICATIONS

Laskowski, "What's a normal resting heart rate", Mayo Clinic, [https://www.mayoclinic.org/healthy-lifestyle/fitness/expert-answers/heart-rate/faq-20057979] published Aug. 29, 2018 (Year: 2018).*

*Primary Examiner* — Eugene T Wu
(74) *Attorney, Agent, or Firm* — Hoffberg & Associates; Steven M Hoffberg

(57) ABSTRACT

An individual monitoring device includes a main body provided with a display screen, a bracelet linked to the main body, a measurement instrument to be positioned opposite a radial artery of the wrist of the user, a processor and a location device. The location device includes a geolocation sensor, an avalanche victim detector and a communications device configured to communicate with a beacon. The device monitors against drowning of a child and includes a first sensor to measure a first parameter physiological parameter of the child, and a second sensor to measure a second physiological parameter of the child. The processor is configured to analyze the first physiological parameter and the second measured physiological parameter, and output information indicating the detection or the non-detection of an anomaly based on the analysis of the first and second physiological parameters.

18 Claims, 7 Drawing Sheets

(51) Int. Cl.
*A61B 5/0205* (2006.01)
*A61B 5/024* (2006.01)
*A61B 5/026* (2006.01)
*A61B 5/145* (2006.01)
*G08B 21/02* (2006.01)
*G08B 21/08* (2006.01)
*G16H 40/67* (2018.01)

(52) U.S. Cl.
CPC .............. *A61B 5/024* (2013.01); *A61B 5/026* (2013.01); *A61B 5/14542* (2013.01); *A61B 5/7246* (2013.01); *A61B 5/742* (2013.01); *A61B 5/746* (2013.01); *G08B 21/0211* (2013.01); *G08B 21/0288* (2013.01); *G08B 21/088* (2013.01); *G16H 40/67* (2018.01); *A61B 2503/06* (2013.01); *A61B 2562/0219* (2013.01); *A61B 2562/0247* (2013.01); *A61B 2562/0271* (2013.01); *A61B 2562/029* (2013.01)

(58) Field of Classification Search
CPC ................. A61B 5/7246; A61B 5/746; A61B 2562/0219; A61B 2562/0247; A61B 2562/0271; A61B 2562/029
See application file for complete search history.

(56) References Cited

U.S. PATENT DOCUMENTS

| | | | |
|---|---|---|---|
| 2008/0150733 A1 | 6/2008 | Snyder et al. | |
| 2009/0280705 A1 | 11/2009 | Puls et al. | |
| 2009/0322513 A1* | 12/2009 | Hwang | H04W 4/90 600/301 |
| 2010/0081940 A1* | 4/2010 | McKenna | A61B 5/02007 600/479 |
| 2013/0030307 A1* | 1/2013 | Rajan | A61B 5/0024 600/479 |
| 2015/0335283 A1* | 11/2015 | Fish | A61B 5/02416 600/509 |
| 2015/0373521 A1 | 12/2015 | Olesen et al. | |
| 2016/0106326 A1* | 4/2016 | Bajaj | A61B 8/06 600/504 |
| 2016/0228010 A1* | 8/2016 | Kim | A61B 5/021 |
| 2017/0105676 A1 | 4/2017 | Liu | |
| 2017/0231598 A1* | 8/2017 | Baek | A61B 8/54 600/454 |
| 2017/0238817 A1* | 8/2017 | Lading | A61B 5/6824 |
| 2017/0251930 A1* | 9/2017 | Machida | A61B 5/0059 |
| 2018/0000418 A1* | 1/2018 | Li | A61B 5/6844 |
| 2018/0192896 A1* | 7/2018 | Kato | A61B 5/6843 |
| 2019/0066478 A1 | 2/2019 | Reich et al. | |
| 2019/0290216 A1* | 9/2019 | Koyama | A61B 5/02055 |
| 2020/0093015 A1 | 3/2020 | Seo et al. | |
| 2020/0093378 A1 | 3/2020 | Lange et al. | |
| 2020/0126391 A1* | 4/2020 | Lovett | G08B 25/10 |

FOREIGN PATENT DOCUMENTS

| | | |
|---|---|---|
| GB | 2 408 893 A | 6/2005 |
| JP | 6 044753 B2 | 12/2016 |
| WO | 2018/114180 A1 | 6/2018 |

* cited by examiner

CONNECTED BRACELET TYPE DEVICE FOR INDIVIDUAL MONITORING AND METHOD FOR MONITORING A USER

RELATED APPLICATION

This application claims priority from French Patent Application No. 20 04049 filed Apr. 23, 2020 and No. 20 04051 filed Apr. 23, 2020, each of which is incorporated herein by reference in its entirety.

TECHNICAL FIELD

The present invention relates to the field of individual monitoring devices.

More particularly, the invention relates to a smartwatch allowing performing a monitoring of a user when the latter evolves in a potentially hazardous environment, for example a trekker, a climber, a skier, a person practicing climbing in a natural environment, whether for professional purposes or not. The invention also relates to the field of tracking in such hazardous environments.

More particularly, the invention also relates to a device for monitoring persons, in particular children, in the form of a bracelet intended to be worn by a child at his wrist and adapted to output information indicating an anomaly in case of danger for the child, in particular in case of drowning.

Such an invention may also be suitable as a device for individual protection against drowning for other age categories, for example for teenagers, adults, and even seniors.

BACKGROUND OF THE INVENTION

Relatively hazardous environments such as mountains (whether in summer or in winter), forests, trekking paths or natural climbing tracks are known to pose a considerable risk in particular because of the conditions, often hard, for accessing thereto by rescue teams.

Indeed, even when known where a person shall be recovered, which is not always obvious because of the sparse network in a given location and therefore of the difficulty to have an accurate location, intervention teams are often slowed down by the conditions of evolution (terrain, weather conditions, . . . ) which make that every minute saved might turn out to be important.

Moreover, a person wishing to venture out in such environments is likely to have a health problem which might quickly turn out to be dangerous if he/she is too isolated.

In order to be able to anticipate these possible problems, there is therefore a need to implement a device for monitoring and prevention in hazardous environments which is safe, reliable, and which is further resistant enough to withstand, for example, falls or avalanches.

Such a solution may be provided by a smartwatch. Nowadays, the use of smartwatches is becoming common. Therefore, these watches have become more and more functional. For example, there are known connected bracelets allowing communicating by audio or video, or sending messages. There are also known connected bracelets used as monitoring devices, and including one or several sensor(s) allowing measuring for example the pulse rate of a person, his/her calorie expenditure during a physical exercise, or external data such as temperature, ambient humidity, or location using satellite data.

The advantage of such smartwatches lies in that they are attached to a wrist and they are relatively resistant, for example to falls or to weather conditions.

Nonetheless, to date, such smartwatches do not allow performing an accurate monitoring, since in case of impossible access to a network, such a smartwatch will not be geolocated accurately. Furthermore, such watches allow performing measurements in order to display them on a screen but they do not carry any processing of these data in order to alert rescue teams when needed.

Hence, there is a need to improve such smartwatches, and in particular to adapt them to a use in environments that might pose a risk for people health.

There is also a need to provide such a smartwatch that is simple to use and inexpensive to implement, so that the largest number of patients could benefit from it.

On the other side, Accidental drownings cause several hundreds of deaths every year in France. For example, this may consist of a malaise or of a hydrocution.

For children, in particular young children, these constitute the second cause of accidental death after traffic accidents. When these are not followed by death, quite often, they result in serious sequelae, in particular neurological sequelae.

Even though safety instructions, such as the permanent and close monitoring of young children in all swimming areas, are often applied, and although safety devices are implemented (barriers around swimming areas or equipment worn by children), this is not enough as it is relatively easy for a child to escape the attention of his parents and as every safety device could be circumvented (it is possible to climb over barriers, inflatable armbands can be easily removed or deflated).

There is a need to implement a drowning monitoring and prevention device that is safe, reliable, and which is further difficult to remove by a child.

Such a solution may be provided by a connected type bracelet. Nowadays, the use of connected bracelets is becoming common. Therefore, these bracelets have become more and more functional. For example, there are known connected bracelets allowing communicating by audio or video, or sending messages. There are also known connected bracelets used as monitoring devices, and including one or several sensor(s) allowing measuring for example the pulse rate of a person, his/her calorie expenditure during a physical exercise, or external data such as temperature or ambient humidity.

The advantage of such connected bracelets lies in that they are attached to a wrist and they are relatively difficult to pull off by a child.

Nonetheless, to date, such connected bracelets do not allow performing monitoring, in particular children monitoring, as the measurements and analyses performed by such devices are not based on criteria that would be indicative of a person in danger, in particular in danger of drowning. Thus, such a safety device could generate false alerts (for example, the pulse rate of a child that increases while the latter is simply exercising).

Hence, there is a need to improve such safety devices, and in particular to adapt them to a use in the context of monitoring for preventing drowning.

In particular, it is an objective of the invention to overcome the drawbacks of the prior art.

OBJECT AND SUMMARY OF THE INVENTION

The invention addresses this need by providing a smartwatch type device for individual monitoring, adapted to come into contact with a wrist of a user, comprising a main body provided with a display screen, a bracelet linked to the main body, a measurement instrument configured to be positioned opposite a radial artery of the wrist of the user, when the watch is worn by the user, a processor, and a location device, the measurement instrument comprising:

a first sensor configured to measure the oxygen level at said radial artery of said user;

a second sensor configured ted to measure the heart rate of said user by measuring the vibrations at said radial artery;

a third sensor configured to measure the ascending and descending blood flows at said radial artery;

a fourth sensor configured to measure the cutaneous temperature of said user.

The processor is configured to:

acquire the measured data of said first sensor, second sensor, third sensor and fourth sensor;

analyze the oxygen level measured by said first sensor, comparing said value of the oxygen level with respect to a predetermined first threshold;

analyze the number of vibrations measured by said second sensor, comparing said value of the heart rate with respect to a predetermined second threshold;

analyze the ascending and descending blood flows measured by said third sensor, comparing said value of the ascending blood flow with respect to a predetermined third threshold and of the descending blood flow with respect to a predetermined fourth threshold;

analyze the cutaneous temperature of said user measured by said fourth sensor, comparing said value of the cutaneous temperature with respect to a predetermined fifth threshold; and output information indicating the detection or the non-detection of an anomaly according to said analysis of said oxygen level, heart rate and ascending and descending blood flows of said user, and of said cutaneous temperature of said user.

The location device comprises: a geolocation sensor, an avalanche victim detector, and a communications device configured to communicate with a beacon.

Thus, the invention provides a novel and inventive approach allowing solving at least partially some of the drawbacks of the prior art.

In particular, because this smartwatch could be worn continuously, it allows providing a reliable continuous supervision and also a supervision suited to a use in environments that might be risky to the health of a user.

Moreover, because these measurements are performed at the radial artery of the user, this smartwatch allows obtaining reliable data and performing analyses on accurate data.

Furthermore, thanks to the plurality of implemented sensors as well as the processor, the data can also be cross-checked which enhances this reliability.

Furthermore, such a smartwatch turns out to be simple to use and inexpensive to implement.

According to a feature of at least one embodiment of the invention, said communications device comprise means for receiving a first information output by said beacon, when said beacon is in proximity of said watch, and means for transmitting a second information towards said beacon when said beacon is in proximity of said watch.

Therefore, this allows communicating with the beacons and thus obtaining information as well as communicating information to the beacon. For example, such an embodiment may be useful for a rescue service where a person is to be found, or for a user guidance use.

According to a feature of at least one embodiment of the invention, said first information comprises at least one element amongst the group comprising:

the hour of communication with said beacon;
the date of communication with said beacon;
the location of said beacon; and
a number of persons having received information by said beacon within a predetermined time frame.

According to a feature of at least one embodiment of the invention, said second information comprises at least one element amongst the group comprising:

the hour of communication with said beacon;
the date of communication with said beacon;
an identification number of said smartwatch; and
a characteristic information of said user.

According to a feature of at least one embodiment of the invention, the smartwatch further comprises a sensor adapted to measure an atmospheric pressure and an external oxygen level.

Therefore, this allows coupling the collected data with parameters of the environment in which the smartwatch evolves.

According to a feature of at least one embodiment of the invention, the smartwatch further comprises alert means, if information indicating the detection of an anomaly is output by said output means, said alert means generate an alert message which is transmitted via the communications device to at least one predetermined contact.

The invention also relates to a beaconing system for a smartwatch according to any of the aforementioned embodiments comprising a plurality of passive beacons geographically spaced apart by at least one distance, for alerting emergency services or passing hikers at low frequency, each of said beacons being adapted to communicate with a smartwatch according to any of the aforementioned embodiments, when said smartwatch is worn by a user and is in proximity of said beacon, so that said beacon could output a first information to said smartwatch and receive a second information output by said smartwatch.

Thus, this allows obtaining the position of the user by means of the beacons, for example if the user is in an area in which there is no network, and consequently the geolocation cannot be active. Furthermore, the beaconing system enables the smartwatch to communicate with the beacons and thus obtaining information as well as communicating information to the beacon. For example, such an embodiment may be useful for a rescue service where a person is to be found, or for a user guidance use.

The invention further relates to a method for monitoring a user, said method being adapted to output information indicating the detection or the non-detection of an anomaly, the method implementing a smartwatch adapted to come into contact with a wrist of a user according to any of the aforementioned embodiments, and said method comprising the following steps, implemented by said smartwatch, when said measurement instrument is positioned opposite a radial artery of said wrist of said user:

measurement of the oxygen level of said user, using said first sensor;

measurement of the heart rate of said user by measuring the vibrations at said radial artery, using said second sensor;

measurement of the ascending and descending blood flows at said radial artery, using said third sensor;

measurement of said cutaneous temperature of said user, using said fourth sensor;

analysis of said oxygen level, heart rate and ascending and descending blood flows, and cutaneous temperature of said user, so as to transmit instructions to output information indicating the detection or the non-detection of an anomaly; and output of said information indicating the detection or the non-detection of an anomaly.

The analysis step comprising the following successive steps:

comparison of the measured oxygen level with respect to a first predetermined threshold;

comparison of the measured heart rate with respect to a second predetermined threshold;

comparison of the value of the ascending blood flow with respect to a third predetermined threshold and of the value of the descending blood flow with respect to a fourth predetermined threshold, and comparison of the value of the cutaneous temperature with respect to a fifth predetermined threshold, and instruction to output said information indicating the detection of an anomaly if the oxygen level, and/or the heart rate and/or the ascending and/or descending blood flows and/or the cutaneous temperature of said user respectively exceed the first, second, third, fourth and/or fifth predetermined thresholds.

According to a feature of at least one embodiment of the method, if information indicating the detection of an anomaly is output by said output means, the method comprises the following successive steps:

generation of an alert message by said alert means, and sending of said generated alert message to said at least one predetermined contact, via said communications device.

According to a feature of at least one embodiment of the method, it implements a beaconing system according to the aforementioned embodiment, and, when said smartwatch is in proximity of a beacon, the method comprises a step of receiving a first information output by said beacon and a step of transmitting a second information to said beacon.

The invention further relates to a computer program product downloadable from a communication network and/or stored on a microprocessor-readable medium and/or executable by a microprocessor, characterized in that it comprises program code instructions for the execution of a method for monitoring a user according to any of the aforementioned embodiments, when it is executed on a computer or a mobile terminal.

The invention further relates to a non-transitory terminal-readable storage medium, storing a computer program comprising a set of instructions executable by a computer or a processor to implement the method according to any of the aforementioned embodiments.

The invention also provides a connected bracelet type device for individual monitoring of a child against drowning, adapted to come into contact with a wrist of a child, comprising a tight main body, a bracelet linked to the main body, and a measurement instrument comprising:

at least one first sensor configured to measure a first physiological parameter of said child; and at least one second sensor configured to measure a second physiological parameter of said child.

The measurement instrument being located on said bracelet, on a surface of the bracelet disposed opposite said main body, said measurement instrument being configured to be positioned opposite a radial artery and/or radial vein of the wrist of the child, when the bracelet is worn by the child, The device comprising a processor configured to:

analyze the measured first physiological parameter;

analyze the measured second physiological parameter, and output information indicating the detection or the non-detection of an anomaly according to said analysis of said measured first and second physiological parameters.

Thus, the invention provides a novel and inventive approach allowing solving at least partially some of the drawbacks of the prior art.

Indeed, such a connected bracelet allows performing monitoring, in particular children monitoring, based on criteria that would be characteristic of a person in danger, in particular in danger of drowning.

Furthermore, thanks to the combination of the sensor and of the analysis of the measured data, such a drowning monitoring and prevention device turns out to be safe, reliable, and what is more difficult to remove by a child.

According to a feature of at least one embodiment of the invention:

the measured first physiological parameter is analyzed by comparing said value of the first physiological parameter with respect to a first range of predetermined values, and the measured second physiological parameter is analyzed by comparing the value of the second physiological parameter with respect to a second range of predetermined values.

According to a feature of at least one embodiment of the invention, the first sensor and the second sensor are distinct sensors configured to measure a physiological parameter belonging to the group comprising:

the oxygen level in the blood;

the heart rate;

the color of the blood;

the velocity of the ascending blood flow;

the velocity of the descending blood flow;

the cutaneous temperature;

the cutaneous impedance;

the respiratory rate, or a combination of these parameters.

In this instance:

the first sensor is a sensor measuring the oxygen level in the blood, the first range of values being between 80% and 90%, and the second sensor is a sensor measuring the heart rate, the second range of values being between 65 and 90.

According to a feature of at least one embodiment of the invention, the device comprises at least one third sensor adapted to measure a third ambient parameter, the processor including means for analyzing the measured third ambient parameter.

In this instance, said third sensor is a pressure sensor.

According to a feature of at least one embodiment of the invention, the device further comprises a sensor belonging to the group comprising: a geolocation sensor, a humidity sensor and a temperature sensor.

According to a feature of at least one embodiment of the invention, the processor also comprises means for alerting if information indicating the detection of an anomaly is output by said output means.

According to a feature of at least one embodiment of the invention, the device comprises means for manual activation of the monitoring.

According to a feature of at least one embodiment of the invention, the processor also comprises means for remote transmission of said information indicating the detection or the non-detection of an anomaly output by said output means.

According to a feature of at least one embodiment of the invention, the device comprises an electric power supply.

The invention also relates to a method for individual monitoring of a child against drowning, said method being adapted to output information indicating the detection or the non-detection of an anomaly, characterized in that it implements a connected bracelet type device for individual monitoring of said child against drowning adapted to come into contact with a wrist of said child according to any of the embodiments of the invention, and in that said method comprises the following steps, implemented by said monitoring device, when it is in contact with said wrist of said child:

measurement of a first physiological parameter of said child, using the first sensor;

measurement of a second physiological parameter of said child, using the second sensor;

analysis of the first and second physiological parameters of said child, so as to transmit instructions to output information indicating the detection or the non-detection of an anomaly;

output of the information indicating the detection or the non-detection of an anomaly.

According to a feature of at least one embodiment of the method, the step of analyzing the first and second physiological parameters of the child comprises the following substeps:

processing of the first physiological parameter;
comparison of the first physiological parameter with respect to the first range of predetermined values;
processing of the second physiological parameter;
comparison of the second physiological parameter with respect to a second range of predetermined values, and
instruction to output the information indicating the detection of an anomaly if said first and second physiological parameters are not within said first and second ranges of predetermined values respectively.

The invention further relates to a computer program product downloadable from a communication network and/or stored on a microprocessor-readable medium and/or executable by a microprocessor, characterized in that it comprises program code instructions for the execution of a method for individual monitoring of a child against drowning according to any of the aforementioned embodiments, when it is executed on a computer or a mobile terminal.

The invention further relates to a non-transitory computer- or mobile terminal-readable storage medium, storing a computer program comprising a set of instructions executable by a computer or a processor to implement the method according to any of the aforementioned embodiments.

Finally, the invention relates to a system for individual protection against drowning comprising a bracelet according to any of the aforementioned embodiments, and at least one armband adapted to fit around the arms of a child.

BRIEF DESCRIPTION OF THE DRAWINGS

Other objects, features and advantages of the invention will appear clearly on reading the following description, provided as a mere illustrative and non-limiting example, with reference to the figures, amongst which.

DETAILED DESCRIPTION OF EMBODIMENTS OF THE INVENTION

The general principle of the invention is based on the implementation of a smartwatch, adapted to come into contact with a wrist of a user, comprising a main body provided with a display screen, a bracelet linked to the main body, a measurement instrument intended to be positioned opposite a radial artery of the wrist of the user, when the watch is worn by the user, a processor and a location device, the watch being adapted to indicate the detection or the non-detection of an anomaly according to several criteria that are measured at this radial artery.

Such a watch allows performing a coherent analysis of the vital data thanks to a combination of sensors, and thus determining the condition of a person. It also allows obtaining an accurate position of the user at a given time regardless of the conditions of evolution. For example, this determination may allow performing live diagnostics by rescue services, locating a person in trouble.

For example, such a smartwatch may be useful to perform a monitoring of persons who go trekking, in the mountain, skiing, or for any person having to evolve in conditions that might be risky.

This type of devices turns out to be simple to design and to use.

Figure 1:
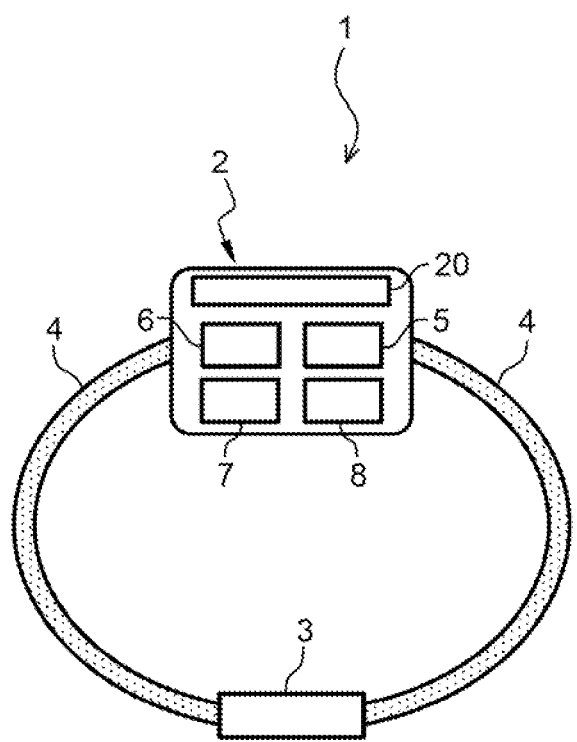
FIG. 1 is a diagram illustrating a side view of a smartwatch according to one embodiment.
Figure 2:
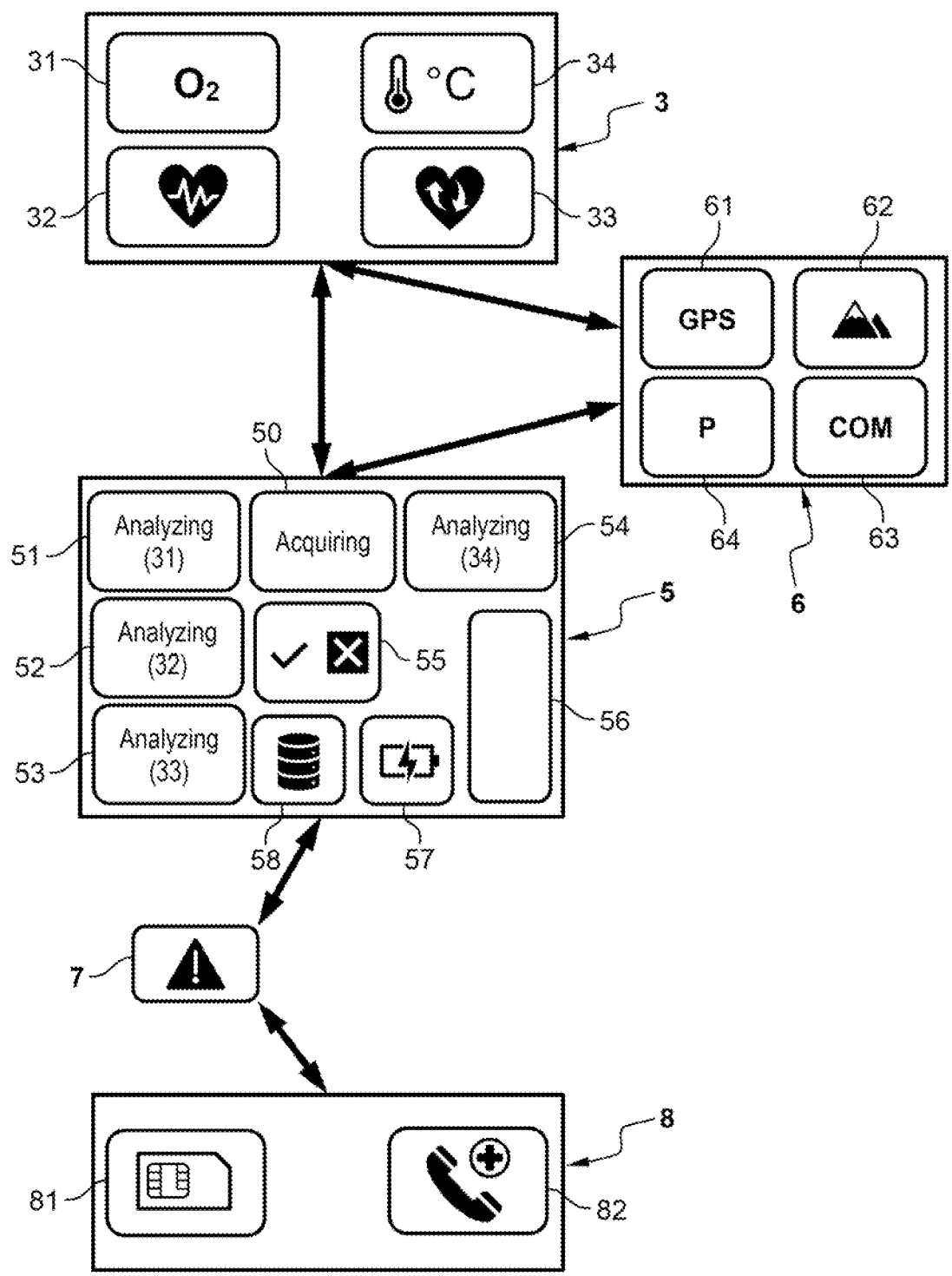
FIG. 2 is a diagram illustrating the different components contained within the smartwatch according to the embodiment of FIG. 1.

A first embodiment of the smartwatch according to the invention is now presented with reference to FIGS. 1 and 2.

As illustrated in these figures, the smartwatch 1 according to this embodiment comprises a main body 2 provided with a display screen 20, a bracelet 4 linked to the main body 2, a measurement instrument 3, a processor 5, and a location device 6.

As described, this watch is adapted to come into contact with a wrist of a user, so that one of the portions, more particularly the portion of the watch where a measurement instrument 3 is housed, could be positioned opposite a radial artery of the wrist of the user, when the watch is worn by this user.

In this embodiment, such a main body 2 is made by injected plastic molding so as to provide a material that is tight and resistant to the different conditions in which the watch might have to evolve, such as in extreme-temperature areas or high-altitude areas.

There may also be provided a main body made of another material that allows providing the same resistance and tightness conditions.

The bracelet 4 may also be made by injected plastic molding or of silicone.

For example, this bracelet may have a closure positioned on one side, so as to facilitate placement and removal thereof.

Nonetheless, the bracelet may also consist of a clasp bracelet or a locking bracelet for safety reasons.

It should be noted that the watch presented in this embodiment comprises an electric power supply. Such a power supply is herein in the form of a battery 57, arranged at the processing unit or processor 5, which thus enables this watch to be autonomous.

According to one embodiment, this battery may be a rechargeable cell or not.

Such a battery may further consist of a LiPO battery enabling a quick charging. This battery may be connected to a USB port allowing charging thereof. Charging may also be done by induction so as to avoid a possible intake of water or dust.

Charging such a battery may also be performed by the Sun, so as to provide an ecological solution.

In this case, it may be provided that the solar charging could be done through an associated solar connector, so as to be able to perform emergency charging, for example in the mountain or when trekking. In this manner, this would allow avoiding the smartwatch running out of battery.

As described before, the smartwatch comprises a measurement instrument 3. In this embodiment, this measurement instrument 3 comprises:

- a first sensor 31 configured to measure the oxygen level at the radial artery of said user;
- a second sensor 32 configured to measure the heart rate of the user by measuring the vibrations at the radial artery;
- a third sensor 33 configured to measure the ascending and descending blood flows at the radial artery; and
- a fourth sensor 34 configured to measure the cutaneous temperature of said user.

In this embodiment, and in order to have a permanent supervision of the user, these measurements are continuously performed.

Of course, where appropriate, it may be provided that either one of these measurements is performed periodically, for example, so as to save the power of the battery of the smartwatch.

According to a non-represented embodiment, this measurement instrument may also comprise a sensor allowing detecting a fall of the user, for example an altimeter configured to detect an abrupt change in altitude (herein, the altitude of the wrist).

In order to prioritize essential sensors monitoring the vital functions, it should be noted that one or more of the sensors may, according to one embodiment, be activated or deactivated by an action of the user, for example by a tactile action on the display screen 20 or through a combination of buttons.

In this embodiment, the measurement instrument 3 is connected, via a cable, which is herein a ribbon cable, to a processor 5 whose function is to analyze the measured parameters and output information indicating the detection or the non-detection of an anomaly according to said analysis.

This processor 5 includes herein:

- means 50 for acquiring the measured data of said first sensor 31, second sensor 32, third sensor 33 and fourth sensor 34;
- first means 51 for analyzing the oxygen level measured by said first sensor 31, comparing said value of the oxygen level with respect to a predetermined first threshold;
- second means 52 for analyzing the number of vibrations measured by said second sensor 32, comparing said value of the heart rate with respect to a predetermined second threshold;
- third means 53 for analyzing the ascending and descending blood flows measured by said third sensor 33, comparing said value of the ascending blood flow with respect to a predetermined third threshold and of the descending blood flow with respect to a predetermined fourth threshold;
- fourth means 54 for analyzing the cutaneous temperature of said user measured by said fourth sensor 34, comparing said value of the cutaneous temperature with respect to a predetermined fifth threshold; and
- means for outputting 55 information indicating the detection or the non-detection of an anomaly according to said analysis of said oxygen level, heart rate and ascending and descending blood flows of said user, and of said cutaneous temperature of said user.

According to an embodiment of the invention, the means for outputting 55 information indicating the detection or the non-detection of an anomaly according to the analysis of the oxygen level, heart rate, ascending and descending blood flows, and cutaneous temperature of the user can output information indicating the detection of an anomaly if at least one of the measured parameters is indicative of an anomaly.

For example, in case of an abrupt drop in the oxygen level, perceivable through the measurement of the oxygen level and then the comparison with respect to a predetermined threshold of the expected oxygen level, the output means could output information indicating the detection of an anomaly.

Furthermore, if the comparison of the value of the ascending blood flow with respect to a predetermined third threshold and/or of the descending blood flow with respect to a predetermined fourth threshold reveals an anomaly, this might be indicative of a cardiac pathology (arrhythmia, tachycardia, bradycardia, or heart trouble), the output means could therefore also output information indicating the detection of an anomaly.

In addition, in case of an abrupt drop in the temperature of the user, perceivable through the measurement of his cutaneous temperature and then the comparison with respect to a predetermined fifth threshold of the temperature, the output means could output information indicating the detection of an anomaly, for example a hypothermia.

According to another embodiment, and in order to be able to reduce the possibility of a false alert, the output means could output information indicating the detection of an anomaly if at least two of the measured parameters are indicative of an anomaly, that is to say if at least two of the measured parameters are beyond the respective predetermined threshold.

It should be noted that this processor 5 further comprises means 58 for storing the measured data of the first sensor 31, second sensor 32, third sensor 33 and fourth sensor 34.

Storing the measured data of the first sensor 31, second sensor 32, third sensor 33, and fourth sensor 34 allows keeping a history of vital information of the user over a substantially long period depending on the embodiments. In this manner, a person who consults the history, such as a physician or a nurse in case of intervention of rescue teams, can have a complete overview of the medical history of the user of the smartwatch.

According to one embodiment, the device further comprises means for analyzing the measured data stored over a predefined period, for example to detect possible anomalies, such as a cardiac arrhythmia, a hypertension or a hypothermia.

It should be noted that, according to one embodiment, and for more effectiveness for example in case of intervention of rescue teams, the storage means may further contain at least one information relating to the user belonging to the group comprising: the age of the user, anatomical data of the user, morphological data of the user, the medical history of the user and the blood type of the user.

In this case, and for the response given to a possible anomaly to be the most suitable as possible, it is preferable that:
  the predetermined first threshold is defined according to said at least one information relating to said user, and/or
  the predetermined second threshold is defined according to said at least one information relating to said user, and/or
  the predetermined third threshold is defined according to said at least one information relating to said user, and/or
  the predetermined fourth threshold is defined according to said at least one information relating to said user, and/or
  the predetermined fifth threshold is defined according to said at least one information relating to said user.

For example, a heart rate threshold will not be the same if the person is athletic or not, according to his age or his morphology.

Similarly, the medical history may be useful for medical professionals should these have to perform a surgery. Hence, such a feature may turn out to be useful in case of intervention of rescue teams who might need to access some data of a patient to be able to quickly intervene.

Thus, according to one embodiment, this information relating to the user may be consulted by displaying on the display screen 20 of the main body 2.

For example, this may be accessible through a combination of keys or by pressing on this display screen.

According to one embodiment, one or several information relating to the user may be automatically displayed in case of output of information indicating the detection of an anomaly.

According to the invention, as said before, the smartwatch 1 further includes a location device 6. This location device 6 comprises: a geolocation sensor 61, an avalanche victim detector 62, and a communications device 63 adapted to communicate with a beacon 9.

According to a known technology, the avalanche victim detector 62 is an electronic apparatus for emitting-receiving a particular radio signal, intended to rapidly locate its wearer if the latter is buried under a snow avalanche, by another AVD manipulated nearby by a person coming to rescue. Such an avalanche victim detector can allow emitting this low-energy particular radio signal even when the watch no longer has enough battery for a predetermined time frame, for example during 7 days.

For example, the geolocation sensor 61 enables the user to determine his position in connection with a mapping displayed on the screen 20 of the smartwatch.

This mapping may also comprise a display of an estimated route as well as an estimated time remaining before reaching a geolocation objective input by the user.

It may be provided that the mapping illustrates track color indications, in the case of a use in proximity of a skiing field.

For example, such a mapping may be downloadable via an application, such as a mobile application, which would be paired with such a smartwatch.

It may also be provided that the smartwatch also embeds a compass. In this manner, this allows amplifying the accuracy of the provided indications with regards to the position and to the direction to follow for a user.

It may be imagined an embodiment wherein this location sensor is adapted to share its location with other location sensors of nearby smartwatches so that the mapping displayed on the main screen could display other persons nearby.

It may also be imagined an embodiment wherein the shared locations of the different watches could be synchronized on an application, such as a mobile application, so as to generate a (Waze type) navigation assist mapping. Such a mobile application may be used for climbing, skiing, trekking, or any other activity.

Furthermore, and as described, the location device 6 comprises communications device 63 adapted to communicate with a beacon 9.

Figure 5:
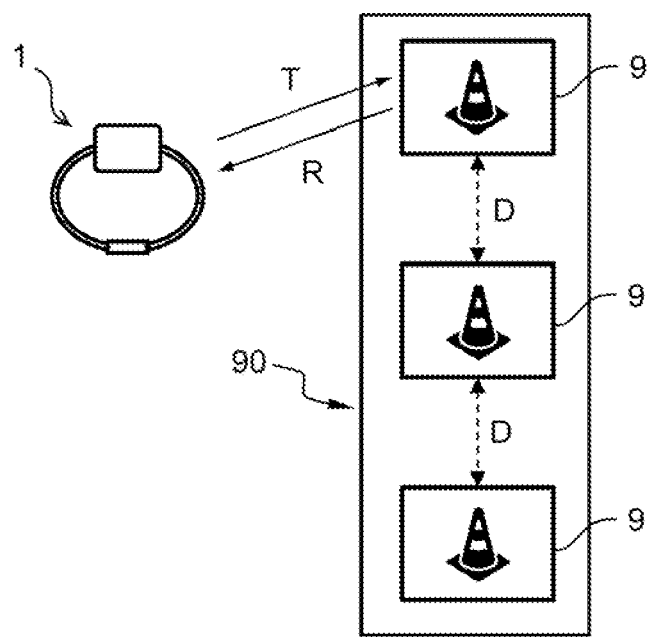
FIG. 5 is a diagram illustrating a beaconing system according to an embodiment of the invention, with a smartwatch according to the embodiment of FIG. 1.

Indeed, for example, if the user is located in an area within which there is no network, and consequently, the geolocation sensor 61 could not be active, the position of the user cannot be obtained by this beacon. Therefore, the smartwatch 1 according to the invention is intended to be able to communicate with a beaconing system 90 as illustrated in FIG. 5.

This beaconing system 90 for a smartwatch comprises a plurality of passive beacons 9 geographically spaced apart by at least one distance D, each of the beacons 9 being adapted to communicate with the smartwatch when the latter is in proximity of the beacon 9 and when it is worn by a user, so that the nearby beacon 9 could output a first information R to the smartwatch 1 and receive a second information T transmitted by the smartwatch 1.

Therefore, the communications device 63 comprise means for receiving the first information and means for transmitting the second information.

For example, the distance D may be equal to 1 km. Therefore, it is possible to determine the exact position of the user within 1 km. It should be noted that between two beacons, the position of the user may be approximated, for example according to an estimate of the speed of the user, of the followed route.

According to a preferred embodiment, this beaconing system may be configured to operate only with this type of smartwatch provided by the invention.

In other words, the described beaconing system may be specific to the smartwatch provided by the invention.

It should be noted that these beacons operate only in a passive way, that is o say they output information to the smartwatch in response to a query of this smartwatch but outputting no information on its own to the smartwatch.

According to the embodiments, the first information comprises at least one element amongst the group comprising:
- the hour of communication with the beacon 9;
- the date of communication with the beacon 9;
- the location of said beacon 9; and
- a number of persons having received information by the beacon 9 within a predetermined time frame.

Furthermore, the second information comprises at least one element amongst the group comprising:
- the hour of communication with the beacon 9;
- the date of communication with the beacon 9;
- an identification number of the smartwatch 1; and
- a characteristic information of the user.

Thus, by beaconing to a given beacon, a user can for example determine the number of persons having gone through this beacon within a given time period. For example, there may be provided a display of a number of persons having beaconed to a given beacon in the last hour. It may also be provide that the first information contains an approximate distance to a person having beaconed to this given beacon within the defined time period. This may also be done by data triangulation.

This may allow that these data could enable a member of the group to be located with respect to the others and, for example to follow them without losing them, in the case of the user belonging to a group.

In the case of a group, it may, for example, be provided that the identification number of the smartwatch or that the characteristic information of the user are recognizable by the entire group (for example, an identical serial number start for the entire group of watches) so as to facilitate use thereof. For example, such a feature may be useful in order to locate such smartwatches, for example within a leisure complex or within mountain ski stations.

It may also be provided that the data acquired by the beacon through the reception of the first information could be accessible to the rescue teams in case of intervention.

It should be noted that, in this embodiment, the smartwatch further comprises a sensor 64 adapted to measure an atmospheric pressure and an external oxygen level, which is herein placed in the location device 6. Nonetheless, this sensor may also be positioned at another location of the smartwatch.

As illustrated in FIG. 2, the smartwatch according to this embodiment further comprises an alert 7. Therefore, if information indicating the detection of an anomaly is output by the output means 55, the alert 7 generates an alert message which is transmitted via communications device 8 for example to a predetermined contact or to a rescue service.

It may be provided that the smartwatch is able to emit at a low frequency via the communications device 8, even when the latter is discharged, so as to be able to be used in case of emergency.

In this instance, the communications device 8 comprise a port 81 configured to receive a SIM card, preferably a nano SIM card.

These communications device may be accompanied with transmission means implemented in the form of an antenna operating by a wireless technology such as Bluetooth, Wifi, 3G, 4G, or 5G.

In this manner, the alert message may be emitted, for example, in the form of a SMS or a voice message sent on the telephone of a person.

This alert message may also be emitted in the form of a notification on a mobile terminal of the predetermined contact.

This alert message may further be accompanied with an alert sent to rescue services so as to gain in effectiveness for the intervention.

According to one embodiment, the alert message may contain important information on the generated alert, for example the measurement that has generated this alert, information relating to the user, the location of the user.

According to one embodiment, the alert message may also be accompanied with a pre-diagnosis so as to guide a person more easily towards the good rescue service, or to directly guide the rescue services.

According to one embodiment, the sent message may also contain a remote access code enabling the rescue services or the predetermined contact to obtain a lot of information contained in the smartwatch such as the beaconing information.

In the presented embodiment, the predetermined contact(s) is/are stored in the storage means.

According to an embodiment of the invention, this predetermined contact may also be automatically displayed on the display screen 20 in case of output of information indicating the detection of an anomaly.

There may be provided an embodiment of the invention wherein the measured data are accessible by the user who, for example by action on the display screen or through a combination of buttons, sends data to rescue teams or to a predetermined contact via the communications device 8 so as to be able to perform a remote diagnostic or to guide the request of the user.

There may also be provided an embodiment wherein the communications device are accompanied with receiving means (not represented herein) so that a third-party, for example a rescue service, could enter data in a format recognized by the watch.

It may also be provided that the smartwatch comprises means for emitting a notification on the digital screen so as to indicate to the user a recommended or non-recommended route, a weather update, . . . .

Advantageously, the smartwatch according to the presented embodiment further comprises unique identification means.

In this manner, this allows securing the smartwatch by limiting access to the data and to its use to one or several authorized person(s). For example, in case of location of such a smartwatch, this allows preventing stealing thereof.

Furthermore, the smartwatch may comprise means for detecting a set-up of this watch on the wrist of the user.

In this manner, this allows avoiding false alerts in case of a suspect measurement while the watch is not placed on the wrist of the user.

According to one embodiment, the communications device may further comprise means 82 for calling in emergency the predetermined contact.

These emergency call means may be implemented in the form of two buttons placed on either side of the main body, the user having to press simultaneously on both buttons to perform this emergency call.

Such emergency call means may also be implemented in the form of one single button, for example a button placed at a location of the smartwatch that is difficult to access so that it could not be used inadvertently.

Figure 3:
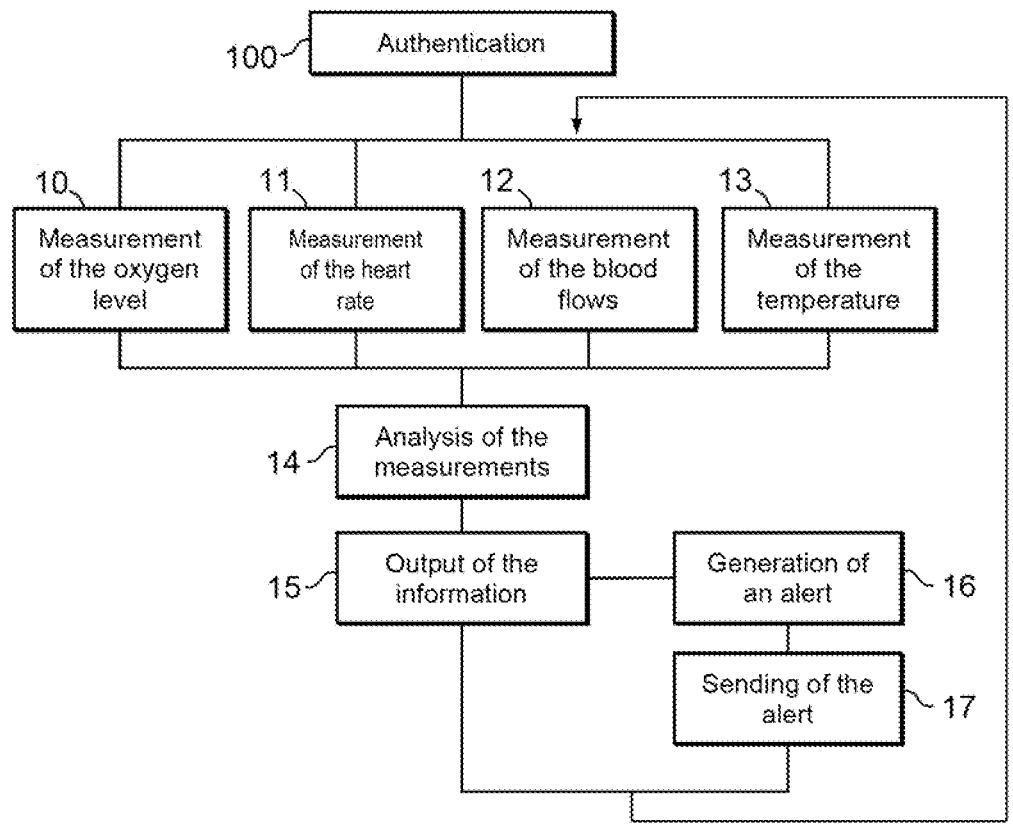
FIG. 3 is a diagram illustrating a method for monitoring a user according to an embodiment of the invention.
Figure 4:
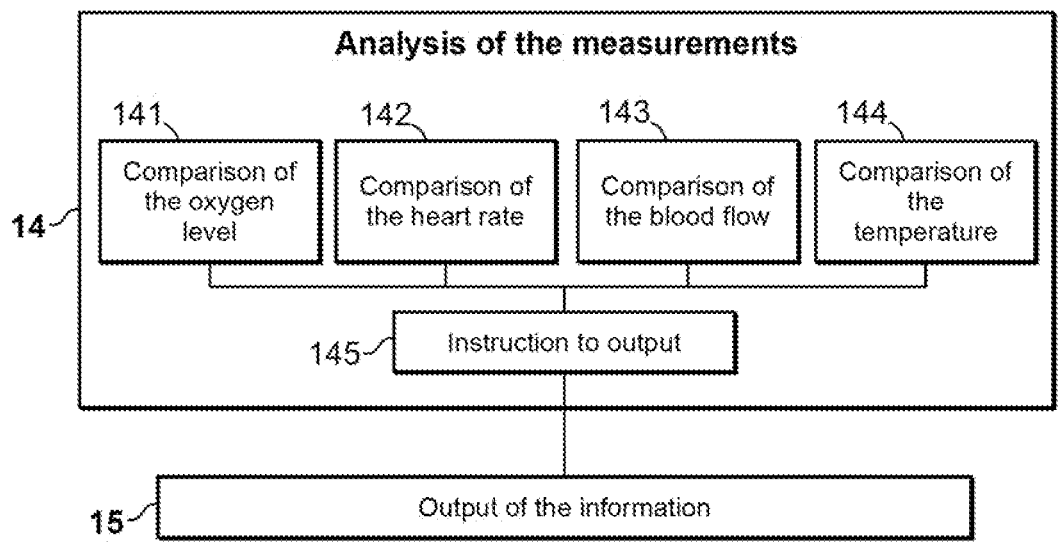
FIG. 4 is a diagram illustrating in detail the analysis step of the method according to the embodiment of FIG. 3.

There is now presented, with reference to FIGS. 3 and 4, a method for monitoring a user, this method being adapted to output information indicating the detection or the non-detection of an anomaly. According to the invention, this monitoring method implements a smartwatch adapted to come into contact with the wrist of a user according to any of the aforementioned embodiments. As illustrated, the method comprises the following steps, implemented by the smartwatch, when the measurement instrument 3 is positioned opposite a radial artery of the wrist of the user:

- measurement 10 of the oxygen level of the user, using the first sensor 31;
- measurement 11 of the heart rate of the user by measuring the vibrations at the radial artery, using the second sensor 32;
- measurement 12 of the ascending and descending blood flows at the radial artery, using the third sensor 33;
- measurement 13 of the cutaneous temperature of the user, which is done using the fourth sensor 34;
- analysis 14 of the oxygen level, heart rate and ascending and descending blood flows, and cutaneous temperature of the user, so as to transmit instructions to output information indicating the detection or the non-detection of an anomaly; and
- output 15 of the information indicating the detection or the non-detection of an anomaly.

According to the invention, the analysis step 14 comprises the following successive steps:

- comparison 141 of the measured oxygen level with respect to a first predetermined threshold;
- comparison 142 of the measured heart rate with respect to a second predetermined threshold;
- comparison 143 of the value of the ascending blood flow with respect to a third predetermined threshold and of the value of the descending blood flow with respect to a fourth predetermined threshold, and
- comparison 144 of the value of the cutaneous temperature with respect to a fifth predetermined threshold, and
- instruction to deliver 145 said information indicating the detection of an anomaly if the oxygen level, and/or the heart rate and/or the ascending and/or descending blood flows of said user respectively exceed the first, second, third, fourth thresholds and/or fifth predetermined threshold.

According to an embodiment of the invention, the step of instructing the output 15 of information indicating the detection or the non-detection of an anomaly according to the analysis of the oxygen level, and/or heart rate and/or ascending and/or descending blood flows and/or cutaneous temperature of the user can output information indicating the detection of an anomaly if at least one of the measured parameters is indicative of an anomaly.

According to another embodiment, and in order to be able to reduce the possibility of a false alert, the output step adapted to output information indicating the detection of an anomaly could be performed if at least two of the measured parameters are indicative of an anomaly, that is to say if at least two of the measured parameters are beyond the respective predetermined threshold.

In the embodiment of the method illustrated in FIG. 3, if information indicating the detection of an anomaly is output by the output means 55, the method comprises the following successive steps:

- generation 16 of an alert message by the alert 7; and
- sending 17 of the generated alert message to the predetermined contact, or to rescue services, via the communications device.

Furthermore, in the illustrated embodiment, the method comprises a prior authentication step 100. In this manner, this allows securing the smartwatch by limiting access to the data and to the use thereof to one or several authorized person(s).

The invention also relates to a computer program product downloadable from a communication network and/or stored on a microprocessor-readable medium and/or executable by a microprocessor, comprising program code instructions for the execution of a method for monitoring the user according to any of the aforementioned embodiments, when it is executed on a computer.

The invention also relates to a non-transitory computer-readable storage medium, storing a computer program comprising a set of instructions executable by a computer or a processor to implement the method for monitoring the user according to any of the aforementioned embodiments.

More particularly, the storage medium may be included in the main body, for example in the memory 58 embedded within the processor. It may also be included within the measurement instrument.

It may also be provided that such a watch comprises, in this memory, a maintenance schedule, so that the offered functions remain optimal and the supervision is reliable for a given user.

The general principle of the invention is based on the implementation of a connected bracelet type device for individual monitoring against drowning, adapted to come into contact with a wrist of a child, and capable of indicating the detection or the non-detection of an anomaly according to an analysis of measured physiological parameters of the child.

Such a bracelet may be used to enhance safety and monitoring of persons, more particularly of vulnerable persons, even more particularly of children, in order to avoid drowning.

For example, such an individual monitoring device may be used in a private or municipal pool, at sea, in water bodies, or everywhere a risk of drowning could arise.

This type of devices turns out to be simple to design and to use.

Figure 6:
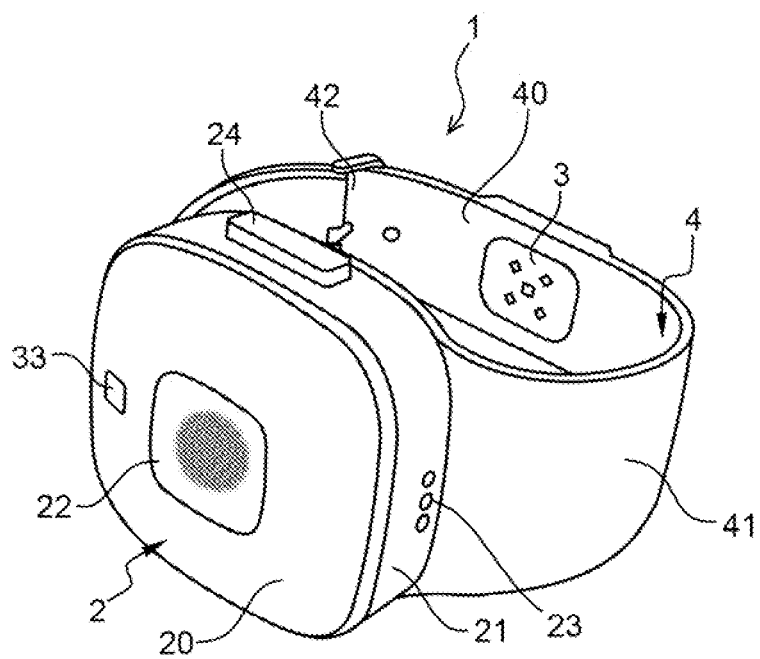
FIG. 6 is a perspective view of a monitoring device according to an embodiment of the invention.
Figure 7:
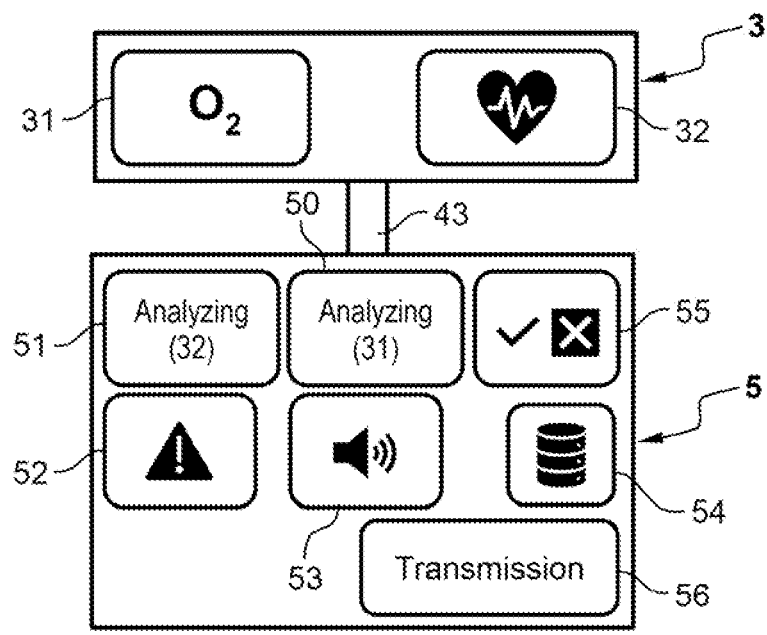
FIG. 7 is a diagram illustrating a measurement instrument and a processor according to an embodiment of the invention.
Figure 8:
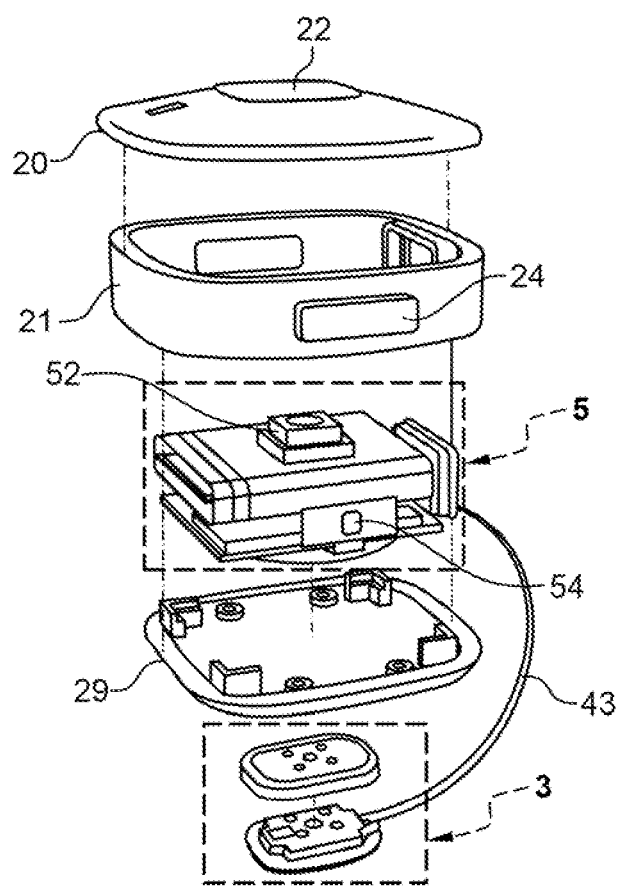
FIG. 8 is an exploded perspective view of a monitoring device according to the embodiment of FIG. 6.

A first embodiment of the monitoring device according to the invention is now presented with reference to FIGS. 6 to 8.

As illustrated, the monitoring device 1 comprises a tight main body 2 and a bracelet 3 linked to the main body 2.

In this instance, the main body 2 has a substantially square shape with rounded angles and is composed by a bottom 29 topped with sidewalls 21, the whole being covered with an upper surface 20 forming a cap.

Of course, there may be provided other embodiments wherein this main body would have another shape. For example, there may be provided a rounded, lozenge-shaped, triangular, or star-shaped main body.

In this embodiment, such a main body 2 is made by injected plastic molding so as to provide a material that is tight and resistant to the different conditions in which it might have to evolve, such as sea water.

There may also be provided a main body made of another material that allows providing the same resistance and tightness conditions.

As regards the bracelet 3 linked to the main body 2, it has a first portion 30 bearing a surface disposed opposite the main body 2 and intended to be positioned opposite a radial artery and/or radial vein of the wrist of the child, when the bracelet is worn by the child, and two second portions 41 each linked by one end to the main body 2, one of the two further bearing the first portion.

The bracelet 3 may also be made by injected plastic molding or of silicone.

In this embodiment, the bracelet 3 is formed by two arms, one of the arms being constituted by one of the two second portions 41 linked to the first portion 40, and the other arm being constituted by the other one of the two second portions 41. This bracelet further has a loop 42 borne by the arm simply constituted by the other one of the two second portions 41 so as to be inserted into one of the holes formed in the first portion 30. Thus, such a device is attached to the wrist of a child in the same way as a conventional strap watch.

Figure 11A:
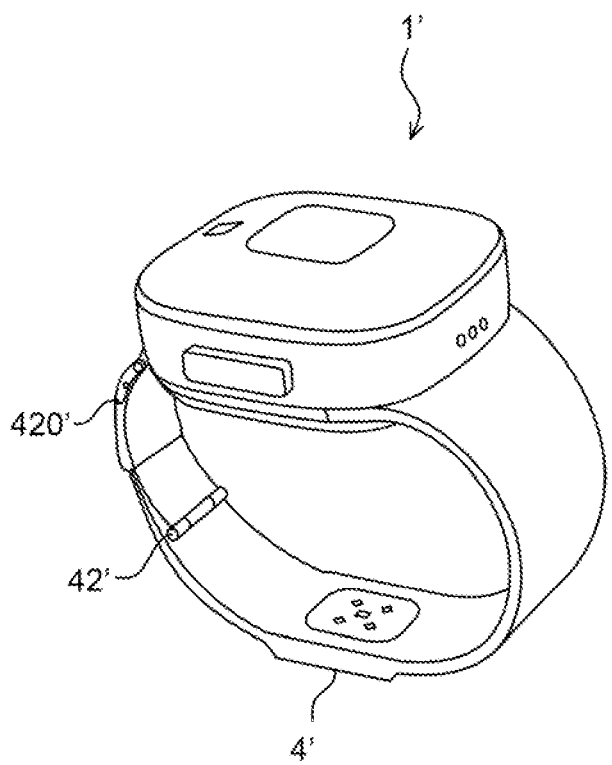
FIG. 11A is a perspective view of a monitoring device according to a second embodiment of the invention.
Figure 11B:
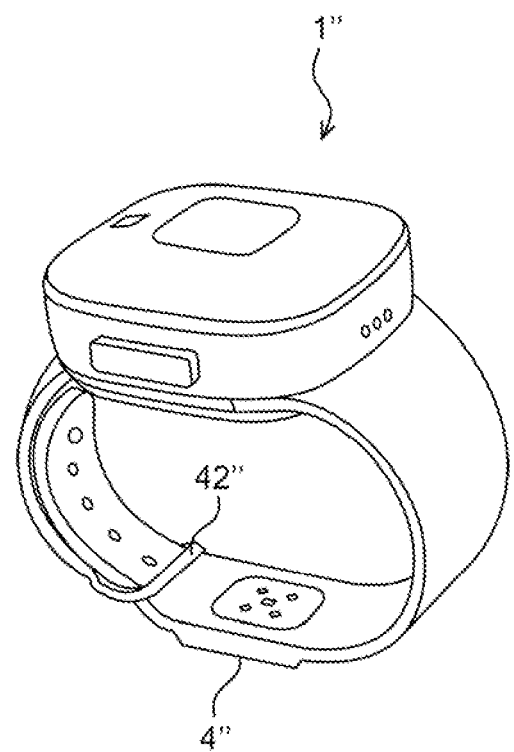
FIG. 11B is a perspective view of a monitoring device according to a third embodiment of the invention.

Other embodiments of the bracelet are presented in FIGS. 11*a* and 11*b*.

In the embodiment of FIG. 11A, the bracelet 4' is a clasp bracelet, so that such a device 4' is attached to the wrist of a child in the same way as a conventional clasp watch. Two pushbuttons 420' disposed on either side of one of the two second portions carrying the clasp enable a child to open this clasp. Therefore, this may allow offering a double safety to avoid a child being able to remove the bracelet.

In the embodiment of FIG. 11B, the bracelet 4" is formed by two arms, one of the arms being constituted by one of the two second portions linked to the first portion, and extended by a third portion and the other arm being constituted by the other one of the two second portions which, when the bracelet is attached to the wrist of the child, is placed on top of the third portion and is attached thereto via a metal pin formed on one of the two portions facing one another which fits into a complementary orifice formed in the other one of the two portions facing one another.

According to the invention, the device further comprises a measurement instrument 4. As illustrated more particularly in FIG. 7, the measurement instrument 4 according to the invention comprises: a first sensor 31 adapted to measure a first physiological parameter of the child, and a second sensor 32 adapted to measure a second physiological parameter of the child.

In the illustrated embodiment, the means 50 for analyzing the measured first physiological parameter compare the value of the first physiological parameter with respect to a first range of predetermined values, and the means 51 for analyzing the measured second physiological parameter compare the value of the second physiological parameter with respect to a second range of predetermined values.

More specifically, in the illustrated embodiment, the first sensor 31 is a sensor measuring the oxygen level in blood, the first range of values being between 86% and 90%. Furthermore, in this instance, the second sensor 32 is a sensor measuring the heart rate, the second range of values being between 65 and 90 beats per minute.

In one embodiment, the first range of values may be defined by a series of thresholds crossed within the same range of values ranging from 80% to 90%, for example a step at 90% then a step at 88% then a step at 86% and so on, bearing in mind that below 80%, a child could be considered as being in hypoxia.

Indeed, when a child drowns, the oxygen level falls on a regular basis. The drowning mechanism in children is not the same as for adults, because the child drowns by inhaling water, this may therefore consist of drowning by water or of a dry drowning which happens apart from the first drowning. Thus, such a sensor may allow assessing at the time point T the oxygen level exactly when the child drowns but also ahead of the drowning for dry drowning.

In this instance, the first and second sensors will operate according to a light absorbance principle at the radial artery. The absorbance principle will allow determining the oxygen saturation level of a medium, in this instance the blood of the child. Indeed, the amount of light absorbed by a medium is proportional to the concentration of a given chemical species therein according to Beer-Lambert law.

These sensors, which are therefore placed beneath the radial artery, are equipped with a light emitter-receiver and in connection with a processor. The emitter enables the emission of an infrared light and of a red light thanks to two LEDs. These two lights will cross the radial artery intermittently and will be captured by a receiver. Subsequently, the processor constituted herein by a nano-processor, will quantify them. A calculation on the absorbed light amount will allow determining the blood oxygen saturation, by isolating the variations of the artery on the cardiac sensor. The blood saturation (SpO2), is expressed as a percentage and will allow having an estimate of the level. The normal value is between 90% and 100%. The sensor will further allow measuring the heart rate by calculating the ascending and descending flow, by measuring the variation of the different blood flows at the artery. In this instance, the means for analyzing the first parameter are composed by a microprocessor containing an algorithm enabling the data calculation and the oxygen level analysis and the means for analyzing the second parameter are composed by a second microprocessor calculating the dioxygen level to assess heart- and lung-related problems in the second bracelet.

The measurement instrument may have a rounded or square shape, so as to cover the entire surface of the wrist containing the radial artery.

Nonetheless, there may be provided other embodiments wherein the first and second sensors are distinct sensors adapted to measure a physiological parameter belonging to the group comprising:
the oxygen level in the blood;
the heart rate;
the color of the blood;
the velocity of the ascending blood flow;
the velocity of the descending blood flow;
the cutaneous temperature;
the cutaneous impedance;
the respiratory rate, or
a combination of these parameters.

For example, the cutaneous temperature may turn out to be useful to detect a possible hypothermia.

In the illustrated embodiment, this measurement instrument 4 is located on the bracelet 3, over a surface of the portion 30 of the bracelet which is disposed opposite the main body 2. Therefore, the measurement instrument 4 is intended to be positioned opposite a radial artery and/or radial vein of the wrist of the child, when the bracelet is worn by the child.

Such an arrangement is useful to perform accurate measurements of the physiological parameters.

This measurement instrument 4 is connected, via a cable 43, which is herein a ribbon cable, to a processor 5 whose function is to analyze the measured parameters and output information indicating the detection or the non-detection of an anomaly according to said analysis.

According to the invention, and as already described in part, this processor 5 comprises:
means 50 for analyzing the measured first physiological parameter;
means 51 for analyzing the measured second physiological parameter, and
means 55 for outputting information indicating the detection or the non-detection of an anomaly according to said analysis of said measured first and second physiological parameters.

In the described embodiment, the processor 5 also comprises means for alerting 52, 533 if information indicating the detection of an anomaly is output by the output means 55.

These alert means are in the form of a warning buzzer 52 placed opposite orifices 23 implemented on a lateral wall 21 so as to emit an alert sound so that persons proximate to the child could notice that the child is in a dangerous situation. In this embodiment, these alert means also comprise a warning light 52 emitting a light in case of detection of an anomaly, the information may therefore be the light emission. In this instance, such a warning light is implemented in the form of a LED placed opposite an aperture 22 created on the cap 20 and covered by a material that is at least partially transparent. In this manner, a light signal, for example a blinking of the LED could alert persons proximate to the child that the child is in a dangerous situation.

The device according to the embodiment described herein also has means 24 for manually activating the monitoring. In this instance, these means are implemented in the form of two buttons extending from two opposite sides of the sidewall 21 and enabling a person, for example one of the parents of the child, to activate and/or deactivate the monitoring device, and also to activate and/or deactivate the implementation of the monitoring method that will be presented later on.

In one implementation, to activate or deactivate the device, a person shall press simultaneously on both buttons.

Such means for manually activating the monitoring may also be implemented in the form of one single button, for example a button placed at a location of the device that is difficult to access so that it could not be deactivated inadvertently.

Such an activation means may also be implemented in the form of a code to entre in sequence via three buttons or more, so as to secure the activation and the deactivation even more.

According to another aspect of the device as implemented in this embodiment, the processor 5 also comprises means 56 for remote transmission of the information indicating the detection or the non-detection of an anomaly output by the output means 55.

For example, such transmission means 56 may be implemented in the form of an element adapted to emit and receive data by a wireless technology such as Bluetooth, Wifi, 3G, 4G, or 5G. For example, such an element may be associated to a port for a SIM card (SIM, micro Sim, nano SIM) so that this information is emitted in the form of an sms stent to a remote terminal.

According to one variant, these transmission means 56 may also be paired with a remote terminal so as to be able to communicate with an application, for example a mobile application, and send alerts in the forms of notifications.

In the presented embodiment, the device 1 also comprises a third sensor 33 adapted to measure a third ambient parameter, the processor including means for analyzing the measured third ambient parameter.

In this manner, the means for analyzing the third ambient parameter may analyze this third ambient parameter with respect to a third range of predetermined values, in the same way as with the first and second physiological parameters of the child. Consequently, the analysis means are adapted to output information indicative of an anomaly if the first physiological parameter, the second physiological parameter, and the third external parameter are not within the first, second and third ranges of predetermined values, respectively.

It may also be provided that the analysis of the third sensor is done with respect to a predetermined threshold instead of a range of predetermined values.

In this embodiment, the third sensor is a pressure sensor placed over a monolithic silicon chip, so as to provide an ultra-compact and reliable pressure sensor.

In the illustrated embodiment, the third sensor is a pressure sensor. Therefore, if the measured ambient pressure turns out to be too high, this may be caused by, in the case of a drowning risk, a fall in the water which causes this abrupt change in the pressure.

Consequently, if the means for analyzing the third ambient parameter detect that this third parameter is beyond the range of normal pressure values, the normal pressure corresponding for example to the pressure of open air, they will support, in combination with an anomaly if the first physiological parameter and the second physiological parameter are no longer within their range of values, the output of information indicative of an anomaly by the output means.

In one embodiment, it may nevertheless be provided that only two of the sensors are not within their range of values, an anomaly is triggered anyway.

According to one variant, the device may further comprise a sensor belonging to the group comprising: a geolocation sensor, a humidity sensor and a temperature sensor.

For example, such information may allow obtaining further information, on the location of the child, or a more accurate information on the situation of the child.

For example, in the case of an implementation of a geolocation sensor, such information may be taken into account by the processor according to a location of the child with regards to a map stored in a memory indicating potentially risky locations.

It should be noted that the device presented in this embodiment comprises an electric power supply. Such a power supply is herein in the form of a battery, arranged at the processor 5, which thus enables this device to be autonomous. Such a battery may further consist of a LiPO battery enabling a quick charging. This battery may be connected to a USB port allowing charging thereof. Charging may also be done by induction so as to avoid a possible intake of water or dust.

Figure 9:
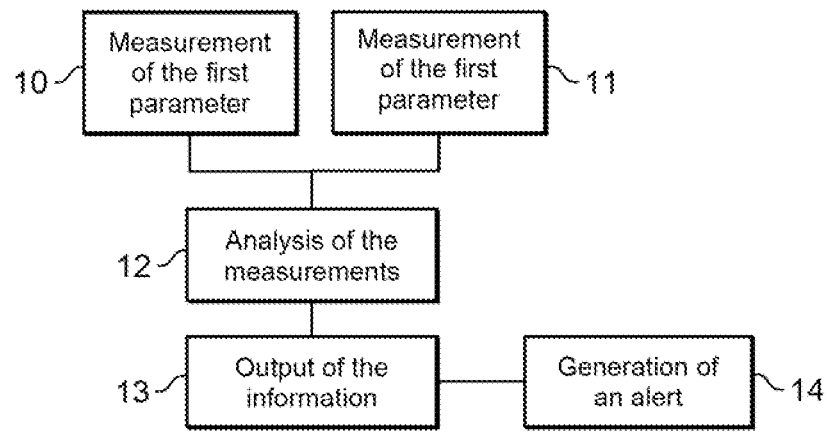
FIG. 9 is a diagram illustrating a method for monitoring a child according to an embodiment of the invention.
Figure 10:
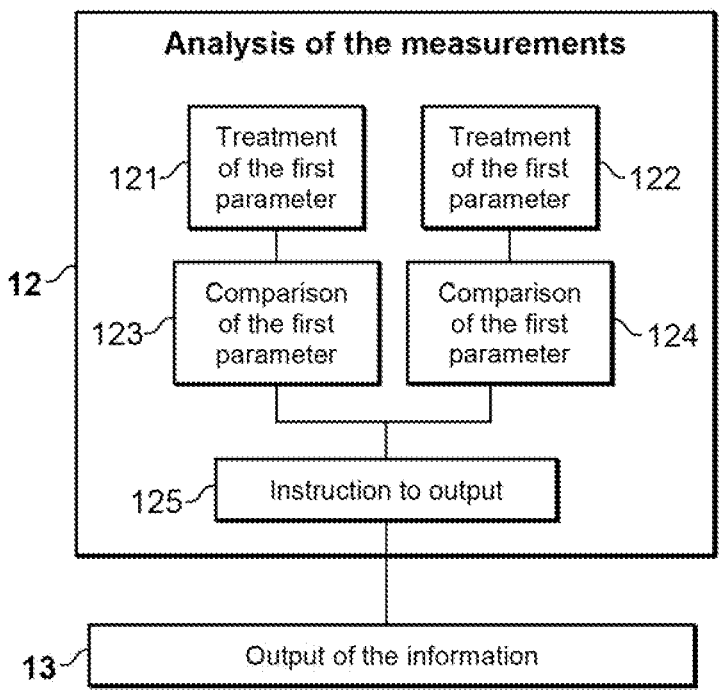
FIG. 10 is a diagram illustrating in detail the analysis step of the supervision method according to the embodiment of FIG. 9.

Next, with reference to FIGS. 9 and 10, a method for individual monitoring against drowning is presented. This method is adapted to output information indicating the detection or the non-detection of an anomaly, which may in particular be indicative of a risk of drowning for a child.

According to the invention, such a method implements a device 1 for individual monitoring against drowning, such as a connected bracelet adapted to come into contact with a wrist of a child according to any of the aforementioned embodiments, and comprises the following steps, implemented by this monitoring device 1, when it is in contact with the wrist of said child (for example, of the child to be monitored):

measurement 10 of a first physiological parameter of the child, using the first sensor 31;

measurement 11 of a second physiological parameter of the child, using the second sensor 32;

analysis 12 of the first and second physiological parameters of the child, so as to transmit instructions to output information indicating the detection or the non-detection of an anomaly; and output 13 of the information indicating the detection or the non-detection of an anomaly.

In other words, the output of the information indicating the detection or the non-detection of an anomaly depends on both first and second physiological parameters of the child.

In this embodiment, the step of analyzing 12 the first and second physiological parameters of the child comprises the following substeps:

- processing 121 of the first physiological parameter;
- comparison 123 of the first physiological parameter with respect to the first range of predetermined values;
- processing 122 of the second physiological parameter;
- comparison 124 of the second physiological parameter with respect to a second range of predetermined values, and
- instruction to output 125 the information indicating the detection of an anomaly if the first and second physiological parameters are not within the first and second ranges of predetermined values respectively.

Thus, if the first physiological parameter of the child, a child in this instance, is beyond the range of predetermined values for this physiological parameter, and if the second physiological parameter of the child is beyond the range of predetermined values for this physiological parameter, then an instruction to output information indicating the detection of an anomaly is emitted by the processor.

For example, this information indicating the detection of an anomaly may consist of an audible alert emitted by the warning buzzer 53, or a visual alert emitted by the LED 52.

It may also consist in the emission of an alert on a remote mobile terminal, for example a smartphone of one of the parents in the case of a child of the bracelet which would be a child, using the transmission means 56.

However, if information indicating the non-detection of an anomaly is output, nothing happens and the method is reiterated.

As already discussed before, the device of the presented first embodiment comprises means for manually activating the monitoring, herein in the form of lateral buttons 24.

Thus, such buttons may allow activating and/or deactivating the implementation of the monitoring method.

It should be noted that, according to a variant of the embodiment, the monitoring method may also comprise a step of deactivation after a determined time frame has elapsed during which it has not been possible to perform any measurement, which indicates that the device is no longer linked to the wrist of a child. For example, such a step may be useful to save the battery of a device.

In a variant of the invention, it may be provided that a child is fitted with an accessory, such as armbands which can be connected to the bracelet by pairing or by wireless communications device.

For example, these armbands may consist of conventional inflatable armbands or armbands having a floating material.

According to one embodiment, such armbands may comprise a sensor adapted to send data to the bracelet, for example at the transmission means 56.

For example, this sensor may be a sensor for detecting set-up on the arms of the child, an alert being sent when it is detected that the child has removed his armbands. According to one variant, such an alert may have an alert distance condition, an alert being emitted when the child gets away from the armbands, for example at 50 cm or 1 m. For example, such a feature could enable an adult to be warned when the child removes his armbands and gets away therefrom.

Such armbands may also be connected to a mobile terminal application.

The invention also relates to a computer program product downloadable from a communication network and/or stored on a microprocessor-readable medium and/or executable by a microprocessor, comprising program code instructions for the execution of a method for individual monitoring against drowning according to any of the aforementioned embodiments, when it is executed on a computer.

The invention also relates to a non-transitory computer-readable storage medium, storing a computer program comprising a set of instructions executable by a computer or a processor to implement the method for individual monitoring against drowning according to any of the aforementioned embodiments.

More particularly, the storage medium may be included in the main body, for example in the memory 54 embedded within the processor.

It may also be included within the measurement instrument.

The invention claimed is:

1. A connected bracelet type device having an identification, configured to come into contact with a wrist of the child and to individually monitor a child against drowning, comprising:
    a main body;
    a display screen in the main body;
    a bracelet linked to the main body;
    at least one first sensor configured to measure an oxygen level at the radial artery of the wrist of the child;
    at least one second sensor configured to measure a heart rate of the child by measuring vibrations at the radial artery of the wrist of the child;
    a third sensor configured to measure ascending and descending blood flow velocities at the radial artery of the wrist of the child;
    a fourth sensor configured to measure a cutaneous temperature of the child;
    at least one processor configured to:
        acquire measured data of the third sensor and the fourth sensor;
        analyze the oxygen level measured by first physiological parameter and compare a value of the oxygen level to a first predetermined threshold,
        analyze a number of vibrations measured by the second sensor and compare a value of the heart rate to a second predetermined threshold,
        analyze the ascending and descending blood flow velocities measured by the third sensor and compare a value of the ascending blood flow velocity to a predetermined third threshold and of the descending blood flow velocity to a predetermined fourth threshold,
        analyze the cutaneous temperature of the child measured by the fourth sensor and compare a value of the cutaneous temperature to a fifth predetermined threshold, and output information on the display screen indicating a detection or a non-detection of an anomaly in accordance with the analysis of the first and second physiological parameters and the detection or the non-detection of the anomaly in accordance with the analysis of the oxygen level, the heart rate, the ascending and descending blood flow velocities of the user, and the cutaneous temperature of the user;
    a satellite data-based geolocation sensor configured to determine a location of the connected bracelet type device; and a first communication device comprising a radio transceiver configured to communicate an alert comprising an indication of the detection of the anomaly, an identification of the connected bracelet type device, and the location of the connected bracelet type device with a beacon, wherein at least one of the at least one first sensor and the at least one second sensor is located on a surface of the bracelet opposite the main body, configured to be positioned on at least one of a radial artery and a radial vein of the wrist of the child to measure a blood flow velocity, when the bracelet is worn by the child.

2. The device of claim 1,
wherein the device comprises a smartwatch; and
wherein the first communications device is configured to receive a first information signal transmitted by the beacon when the beacon is in proximity of the smartwatch and to transmit a second information signal to the beacon when the beacon is in proximity of the smartwatch.

3. The device of claim 2, wherein the first information signal comprises at least one element selected from the group consisting of: hour of communication with the beacon, date of communication with the beacon, a location of the beacon, and a number of people having received information from the beacon within a predetermined time frame.

4. The device of claim 2, wherein the second information comprises at least one element selected from the group consisting of: hour of communication with the beacon, date of communication with said beacon, an identification number of the smartwatch, a characteristic information of the child.

5. The device of claim 1, further comprising a fifth sensor configured to measure at least one of an atmospheric pressure and an external oxygen level.

6. The device of claim 1, wherein the at least one processor is further configured to generate an alert message in response to output of the information indicating the detection of the anomaly, the alert message being transmitted via a second communications device to at least one predetermined contact.

7. The device of claim 1, wherein said at least one first sensor and said at least one second sensor are distinct sensors.

8. The device of claim 1, wherein said at least one first sensor is configured to measure an oxygen level in the blood, wherein the detection or the non-detection of the anomaly is dependent on a threshold between a first range of values being between 80% and 90% saturation; and wherein said at least one second sensor is configured to measure heart rate, wherein the detection or the non-detection of the anomaly is dependent on a threshold between a second range of values being between 65 and 90 beats per minute.

9. The device of claim 1, further comprising at least one fifth sensor configured to measure an ambient parameter; and wherein the at least one processor is further configured to analyze the ambient parameter.

10. The device of claim 9, wherein the fifth sensor is selected from the group consisting of: a pressure sensor, a humidity sensor, and a temperature sensor.

11. The device of claim 1, wherein the radio transceiver is further configured to remotely transmit the information indicating the detection or the non-detection of the anomaly through a 3G, 4G, or 5G wireless technology.

12. A system to provide individual protection against drowning comprising the connected bracelet type device of claim 1 and at least one armband configured to fit around arms of the child having a wireless communication device connected to the connected bracelet type device by wireless pairing.

13. A beaconing system for the device of claim 1, comprising a plurality of passive beacons geographically spaced apart, wherein each passive beacon is configured to communicate with the connected bracelet device worn by the child and in proximity of said each passive beacon, to transmit a first information to the individual monitoring device and to receive a second information transmitted by the individual monitoring device.

14. A method for monitoring a child against drowning, comprising:
placing the device according to claim 1 with the third sensor proximate to the radial artery of the wrist of the child and the main body on an opposite side of the wrist of the child from the radial artery of the child;
measuring the oxygen level of the child by the first sensor;
measuring the heart rate of the child by measuring the vibrations using the second sensor;
measurement of the ascending and descending blood flow velocity of the child by the third sensor;
measuring the cutaneous temperature of the child, using the fourth sensor;
analyzing the oxygen level, the heart rate, the ascending and descending blood flow velocity, and cutaneous temperature of the child by the at least one processor,
the at least one processor successively:
comparing the oxygen level to the first predetermined threshold;
comparing the heart rate to the second predetermined threshold;
comparing the value of the ascending blood flow velocity to the third predetermined threshold;
comparing the value of the descending blood flow velocity to the fourth predetermined fourth threshold; and
comparing the value of the cutaneous temperature to the fifth predetermined threshold;
transmitting instructions to output information indicating the non-detection of the anomaly or the detection of the anomaly in response to at least one of the following: the oxygen level exceeds the first predetermined threshold, the heart rate exceeds the second predetermined threshold, the ascending blood flow velocity exceeds the third predetermined threshold, the descending blood flow velocity exceeds the fourth predetermined threshold, and the cutaneous temperature exceeds the fifth predetermined threshold; and
outputting on the display screen the information indicating the detection or the non-detection of an anomaly.

15. The method of claim 14, wherein in response to the output of the information indicating the detection of the anomaly, further comprising successively:
generating an alert message by the at least one automated processor; and
transmitting the alert message to said at least one predetermined contact via a second communications device.

16. The method of claim 14, further comprising:
providing a plurality of passive beacons geographically spaced apart, wherein each passive beacon is configured to communicate with the device worn by the child and in proximity of said each passive beacon; and
when the individual monitoring device is in proximity of a beacon, the method further comprising:
receiving a first information signal, by the device, transmitted by said beacon; and transmitting a second information to said beacon by the device.

17. A method for individual monitoring of a child against drowning, comprising:
   implementing the connected bracelet type device of claim 1 in contact with a wrist of the child;
   measuring the first physiological parameter of the child by said at least one said first sensor;
   measuring the second physiological parameter of the child by said at least one second sensor;
   analyzing the first and second physiological parameters of the child to transmit instructions to output information indicating the detection or the non-detection of the anomaly; and
   outputting the information indicating the detection or the non-detection of the anomaly.

18. The method of claim 17, wherein the analysis of the first and second physiological parameters of the child comprises:
   processing of the first physiological parameter;
   comparison of the first physiological parameter to a first range of predetermined values;
   processing of the second physiological parameter;
   comparison of the second physiological parameter to a second range of predetermined values; and
   transmission of instructions to output the information indicating the detection of the anomaly in response to the determination that the first and second physiological parameters are not respectively within the first and second ranges of predetermined values.

\* \* \* \* \*